United States Patent
Zaykova-Feldman et al.

(10) Patent No.: US 8,168,949 B2
(45) Date of Patent: May 1, 2012

(54) METHOD FOR STEM SAMPLE INSPECTION IN A CHARGED PARTICLE BEAM INSTRUMENT

(75) Inventors: Lyudmila Zaykova-Feldman, Dallas, TX (US); Thomas M. Moore, Dallas, TX (US); Gonzalo Amador, Dallas, TX (US); Matthew Hammer, Dallas, TX (US)

(73) Assignee: Omniprobe, Inc., Dallas, TX (US)

(*) Notice: Subject to any disclaimer, the term of this patent is extended or adjusted under 35 U.S.C. 154(b) by 68 days.

(21) Appl. No.: 12/896,274

(22) Filed: Oct. 1, 2010

(65) Prior Publication Data

US 2011/0031396 A1 Feb. 10, 2011

Related U.S. Application Data

(62) Division of application No. 12/041,217, filed on Mar. 3, 2008, now Pat. No. 7,834,315.

(60) Provisional application No. 60/925,762, filed on Apr. 23, 2007.

(51) Int. Cl.
*G01N 23/00* (2006.01)

(52) U.S. Cl. .......................... 250/307; 250/310; 702/81
(58) Field of Classification Search .................. 250/307, 250/310; 702/81
See application file for complete search history.

(56) References Cited

U.S. PATENT DOCUMENTS

| | | | |
|---|---|---|---|
| 7,200,506 B2* | 4/2007 | Tomimatsu et al. | 702/81 |
| 7,511,269 B2* | 3/2009 | Munekane | 250/307 |

* cited by examiner

*Primary Examiner* — Phillip A Johnston
(74) *Attorney, Agent, or Firm* — John A. Thomas

(57) ABSTRACT

A method for sample examination in a dual-beam FIB calculates a first angle as a function of second, third and fourth angles defined by the geometry of the FIB and the tilt of the specimen stage. A fifth angle is calculated as a function of the stated angles, where the fifth angle is the angle between the long axis of an excised sample and the projection of the axis of the probe shaft onto the X-Y plane. The specimen stage is rotated by the calculated fifth angle, followed by attachment to the probe tip and lift-out. The sample may then be positioned perpendicular to the axis of the FIB electron beam for STEM analysis by rotation of the probe shaft through the first angle.

5 Claims, 16 Drawing Sheets

METHOD FOR STEM SAMPLE INSPECTION IN A CHARGED PARTICLE BEAM INSTRUMENT

CLAIM FOR PRIORITY

The present application is a divisional of application Ser. No. 12/041,217, filed Mar. 3, 2008, which application claims the priority of U.S. provisional application Ser. No. 60/925,762, filed Apr. 23, 2007 and titled "Method and Apparatus for Cassette-Based In-Situ STEM Sample Inspection;" all of which foregoing applications are incorporated by reference into the present application.

TECHNICAL FIELD

This application relates to TEM sample preparation and inspection inside a charged-particle instrument, such as a dual-beam focused-ion beam microscope, called a "DB-FIB" in this application.

BACKGROUND

The use of focused ion-beam (FIB) microscopes has become common for the preparation of specimens for later analysis in a transmission electron microscope (TEM) or scanning transmission electron microscope (STEM), and the in-situ lift-out technique has become the method of choice for the preparation of a tiny sample for TEM inspection. TEM and STEM inspection offer fine image resolution (<0.1 nm), but require electron-transparent (<100 nm thick) sections of the sample. TEM and STEM inspection usually take place in a separate TEM or STEM device, which requires the transfer of a fragile TEM sample to another location. Dual-beam (DB-FIB) instruments are being more widely used for TEM sample preparation and inspection. The DB-FIB instrument combines high resolution imaging of the SEM with precision, site-specific ion milling of the FIB. The combination of SEM and FIB in the same chamber allows for the location, preparation and inspection of samples in the same microscope. The electron beam within the DB-FIB can substitute for a conventional STEM beam, and a transmitted electron detector, located beneath the sample in the DB-FIB enables in-situ STEM imaging of a sample. As a result, this system provides an increased throughput at reduced cost per sample for failure analysis and process control applications requiring STEM analysis. Applying in-situ lift-out technology in the DB-FIB provides a means for excising tiny samples from a specimen and positioning them on TEM sample holder or grid, using the special features of a nano-manipulator device, for later inspection within the DB-FIB. A suitable nano-manipulator system is the Omniprobe AutoProbe 200™, manufactured by Omniprobe, Inc., of Dallas, Tex.

DRAWINGS

Figure 11:
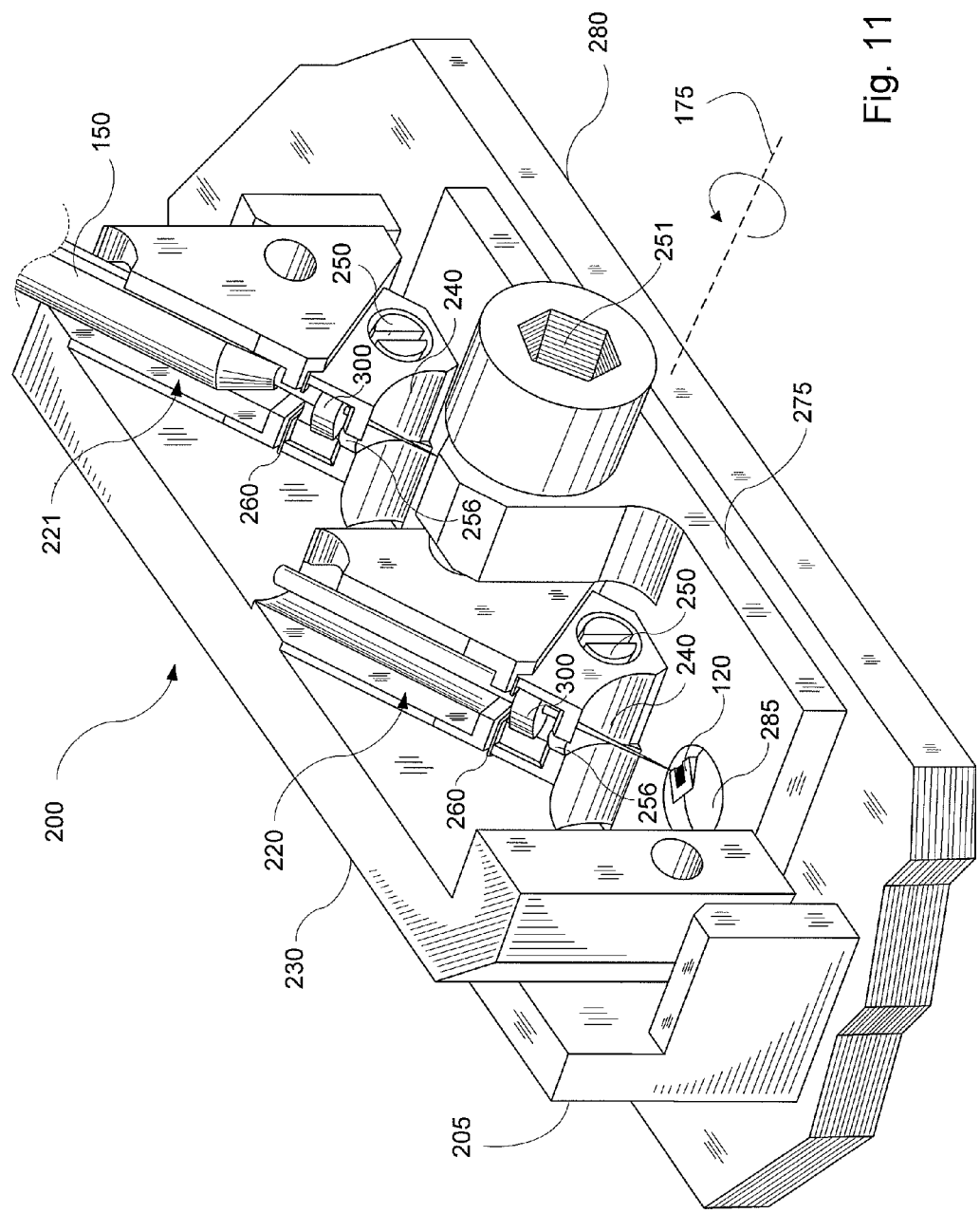

FIG. 11 shows a perspective view of a cassette holding collared probe tips with TEM samples attached. One of the tips shown is held by the gripper of a nano-manipulator. The cassette is shown mounted on a cassette holder.

Figure 12:
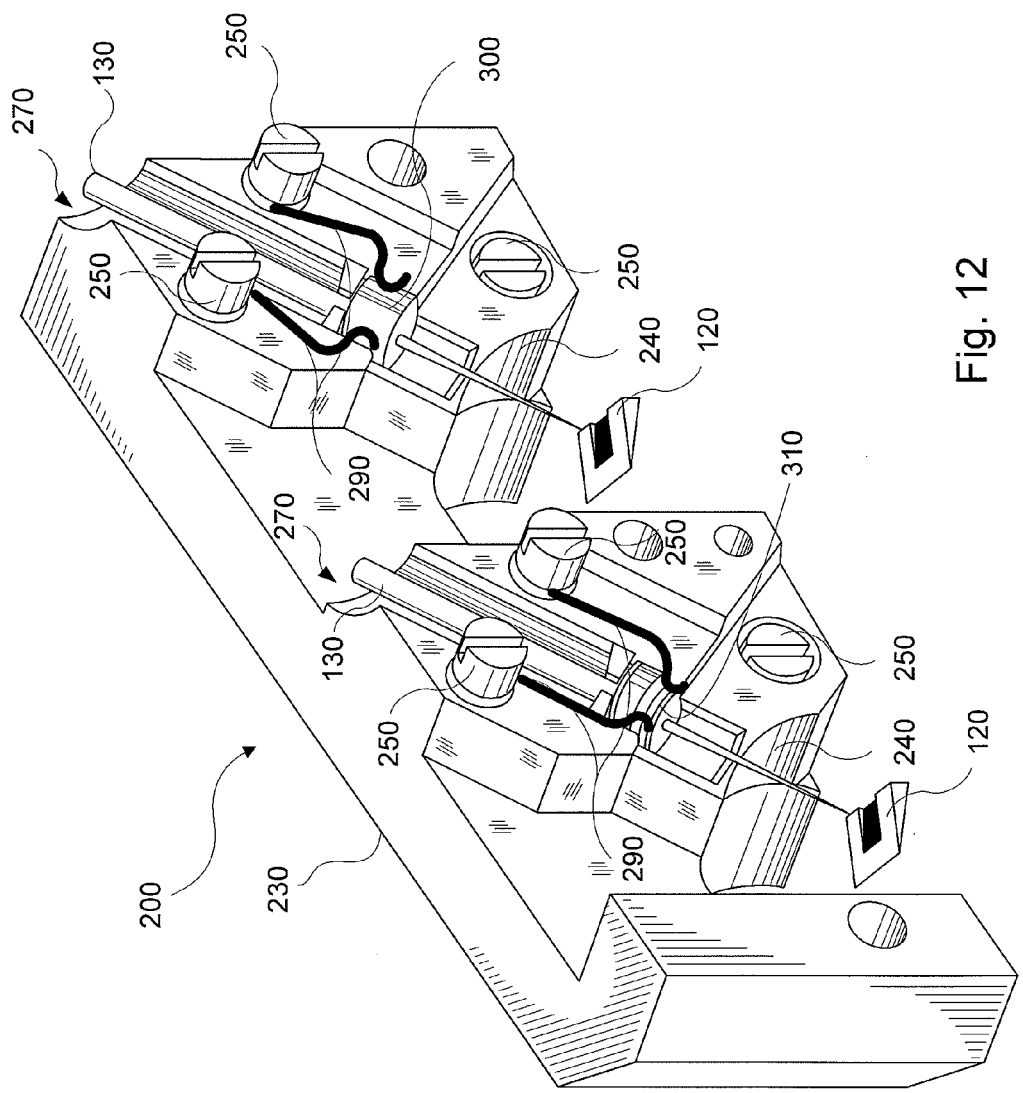

FIG. 12 shows a perspective view of a cassette containing the collared probe tips with TEM samples attached, where the collared probe tips are kept by wire forms. Different embodiments of collars are shown.

Figure 13:
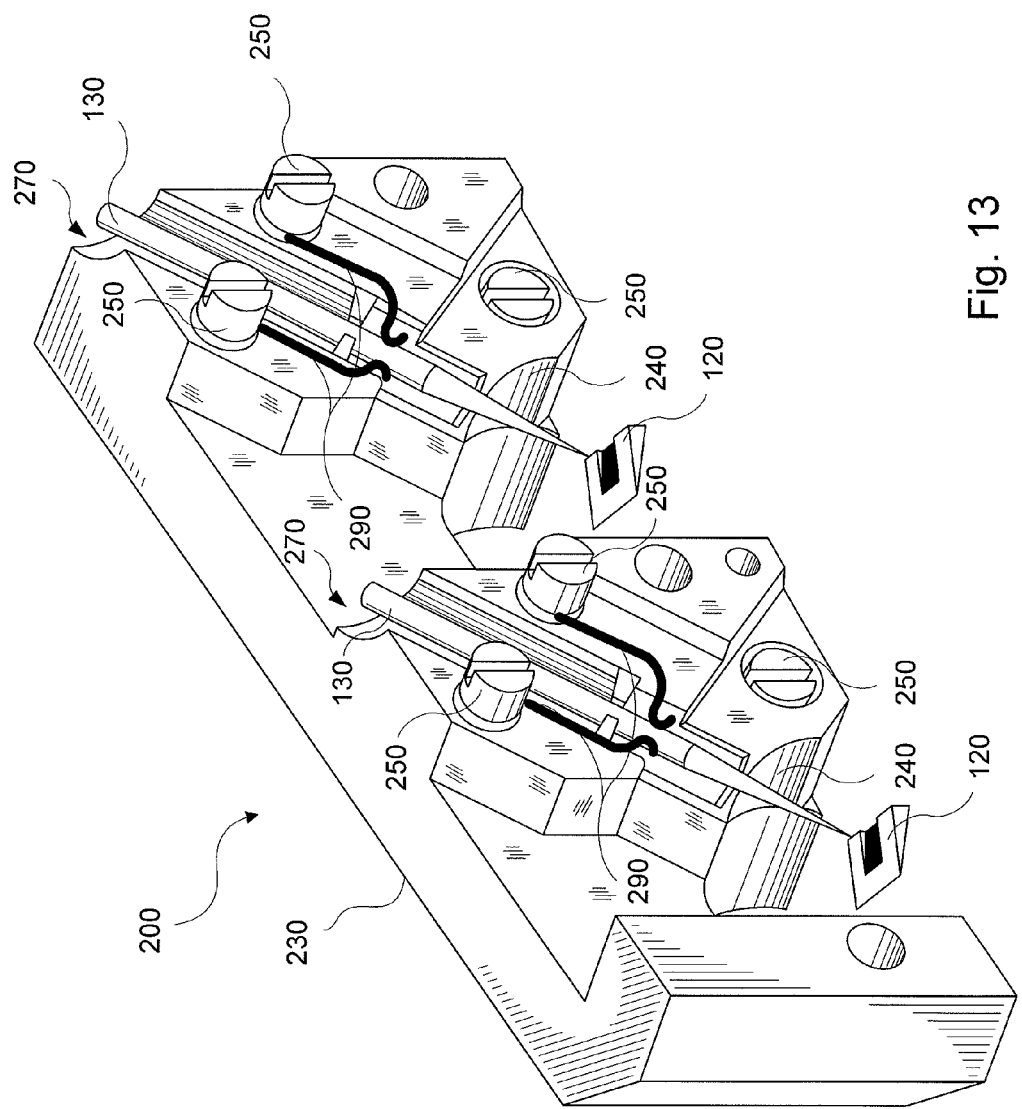

FIG. 13 shows a perspective view of a cassette holding probe tips without collars, where the collars are held in place by a spring means.

Figure 14:
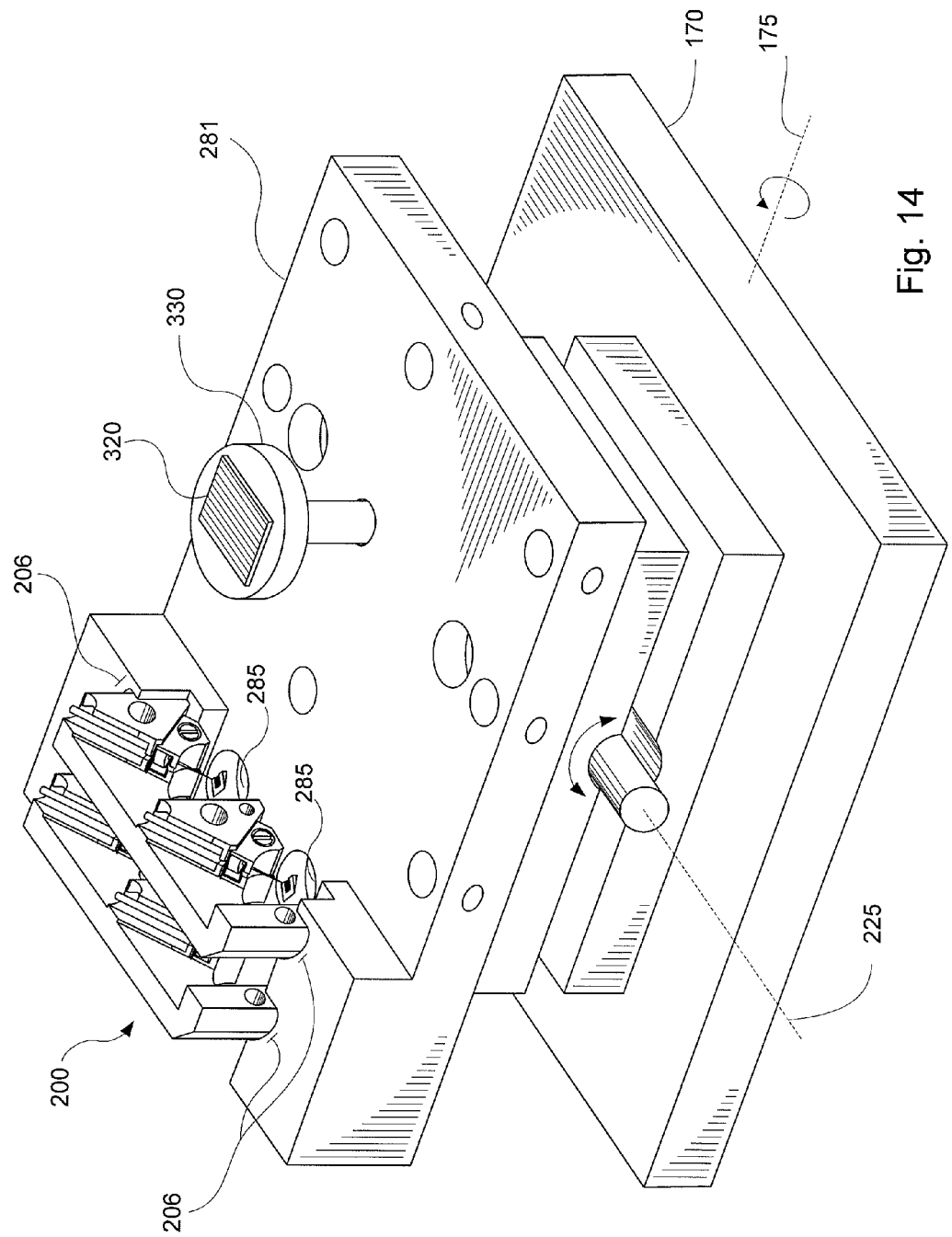

FIG. 14 shows a perspective view of two cassettes connected to a substage of a specimen stage.

Figure 15:
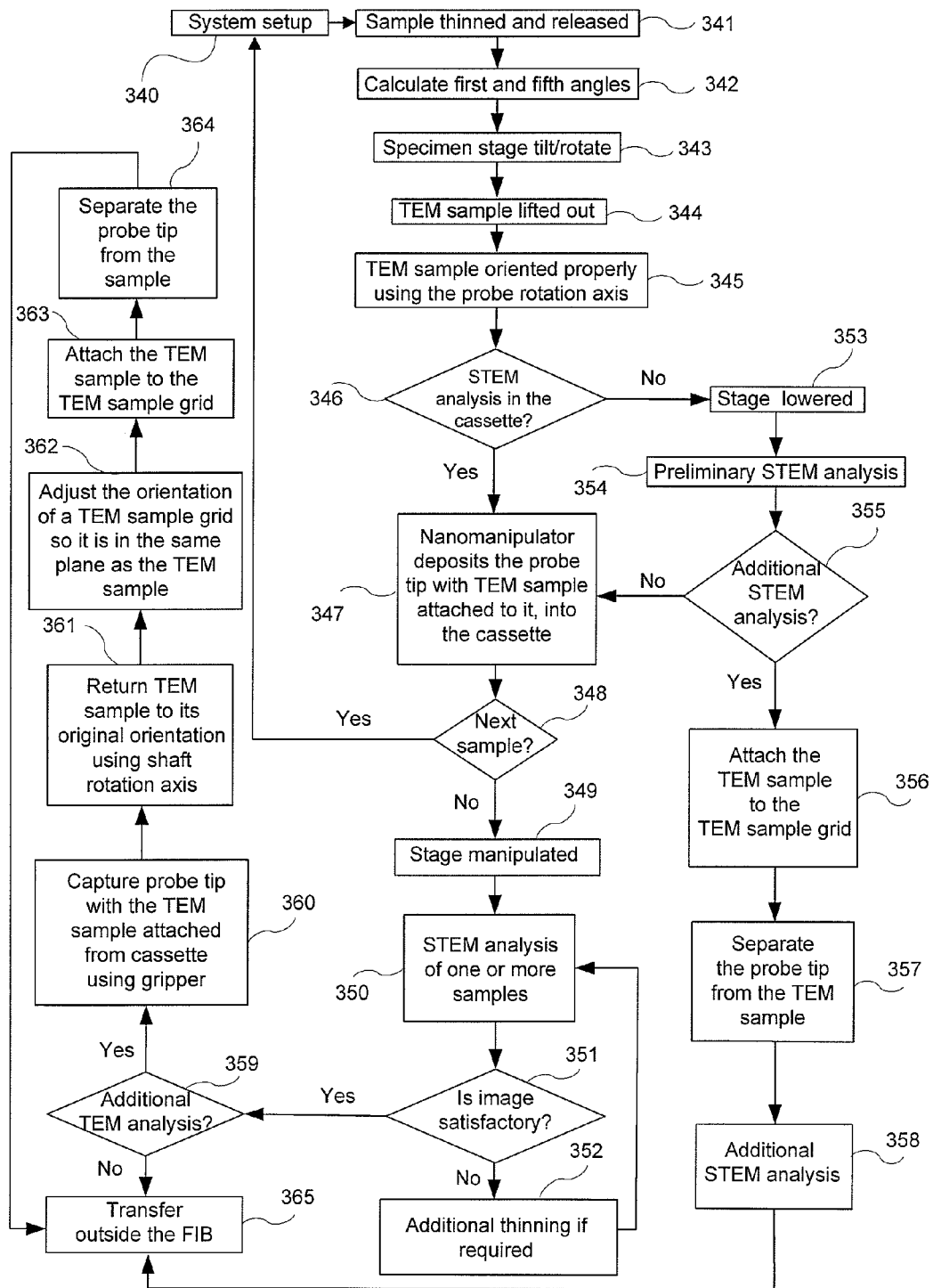

FIG. 15 is a flowchart depicting methods according to the preferred embodiment.

Figure 16:
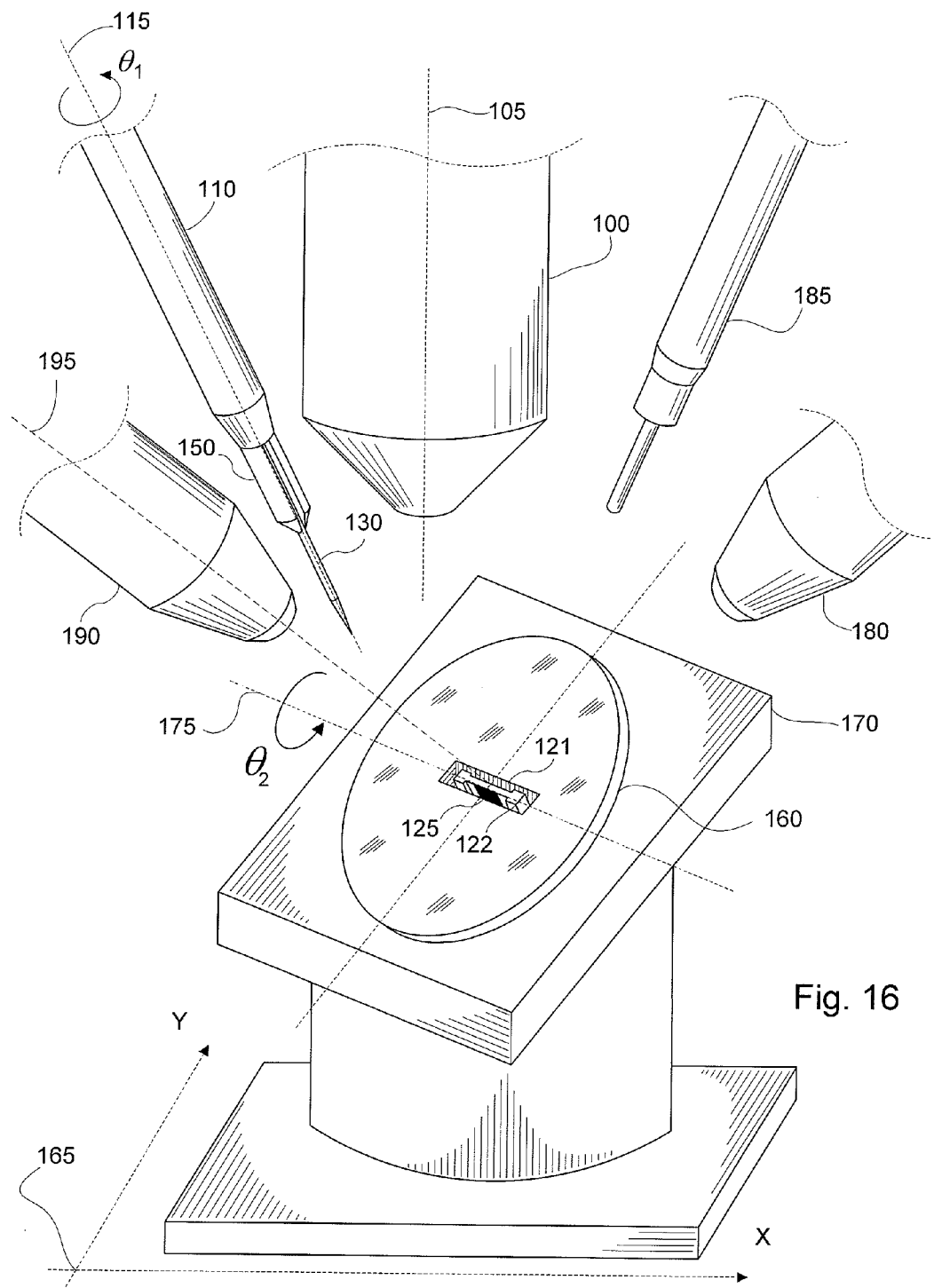

FIG. 16 shows the perspective view of the system according to another embodiment, where the system includes the laser apparatus and a gas injector.

DESCRIPTION

We describe a novel method and apparatus for the process of location, preparation and inspection of samples (120) inside a dual-beam FIB microscope (DB-FIB) using an in-situ probe tip replacement system and a cassette (200) for holding these samples (120). The field of application is not limited to an in-situ probe tip replacement system, dual-beam FIB systems, or to semiconductor samples; applications could include, for example, nano-mechanical systems or biological samples.

Figure 1:
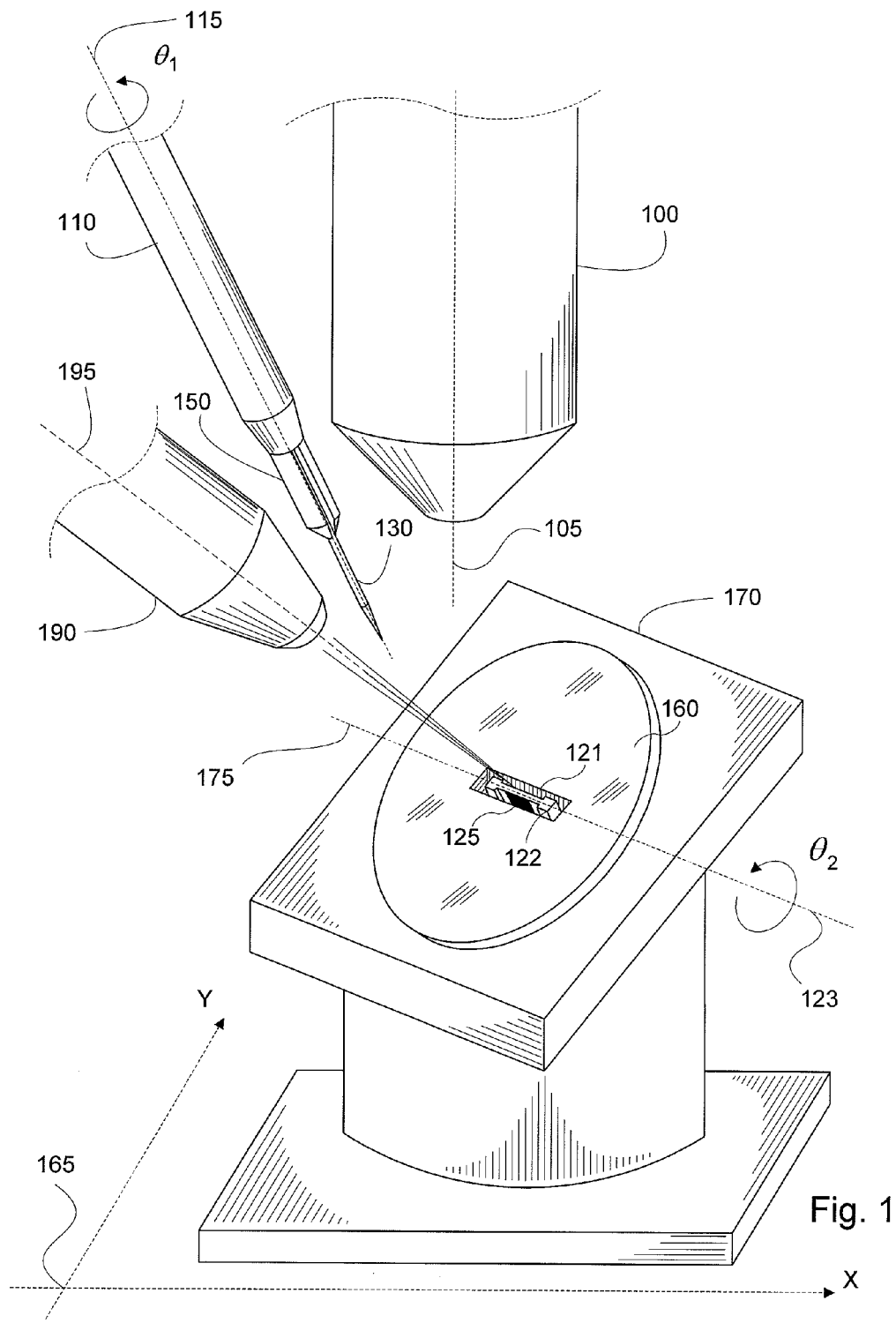
FIG. 1 shows a perspective view of a selectively thinned TEM sample, cut free, but still sitting in its cavity within a specimen.

The method and apparatus of this application provide for higher throughput STEM inspection within the DB-FIB, because the sample does not have to be removed from the microscope. As shown in FIG. 1, the in-situ lift-out process begins in the conventional manner, in which a sample preform (122) is excised from the specimen (160) by ion-beam (190) milling. Such milling may also be performed in particular cases by milling with the electron beam (100) or a laser beam (180) (FIG. 16), with or without assistance from a gas injector (185) (FIG. 16). The specimen stage (170) is tilted to allow a cut around the sample pre-form (122), preferably in a U-shape, and then tilted at another angle for an undercut to free the sample (120). Then, the stage (170) is further translated and rotated to a calculated position for lift-out, as explained below. FIG. 1 shows the stage positioned for milling around the sample pre-form (122), where the tilt axis (175) of the stage (170) is collinear with the long axis (123) of the sample (120). The probe tip (130) may be connected to the released lift-out sample (120) using one of the methods disclosed in U.S. Pat. No. 6,570,170, for example. After reorientation, the sample (120) is then lifted out and disposed at an angle allowing STEM analysis as described in the following disclosure. In all the figures, the size of a sample (120) is exaggerated for clarity.

Method

FIGS. 1-5 show the several stages of lift-out and positioning. Following partial thinning, the released lift-out sample (120) can be manipulated to allow immediate inspection of the area (125) of interest by the e-beam (100) and a transmitted electron detector (210). Obtaining the proper orientation of the sample (120) is aided by a feature typical of DB-FIB sample stages (170) that allows the stage (170) to rotate, tilt, and translate in X, Y, and Z-axes. The sample (120) is cut loose from the specimen, and then the specimen stage (170) is tilted and rotated, as described below. The sample (120) is removed from its trench (121) by the nano-manipulator (140), and after the nano-manipulator shaft is rotated, the sample (120) will have an orientation sufficiently perpendicular to the electron beam (100) axis (105) to be suitable for STEM analysis in the DB-FIB. (Typically the electron beam (100) axis (105) is vertical in the DB-FIB.) If necessary, the sample (120) can be additionally thinned after the lift-out procedure.

Table 1 below shows the mathematical transformations that may be used to determine the correct angles for the DB-FIB sample stage (170) rotation and tilt required to orient the sample (120) for the operations described below. The exemplary calculations shown in Table 1 are a novel application of the well-known conversion from angle-axis representation to rotation-matrix representation. The reader may consult Craig, John J., "Introduction to Robotics Mechanics & Control," Addison-Wesley Publishing Co., 1986, pp. 322-321, for details.

In Table 1, the location of the nano-manipulator probe shaft (110) in the DB-FIB chamber is expressed in terms of a first angle, representing a rotation of the nano-manipulator probe shaft (110) ($\Theta_1$ in the figures); a second angle, being the angle of the stage (170) tilt relative to the X-Y horizontal plane (165) ($\Theta_2$ in the figures); a third angle, being the angle between the projection in the X-Y plane (165) of the axis (115) of the nano-manipulator probe shaft (110) and the extension of the stage (170) tilt axis (175) nearest the front door (135) of the DB-FIB. ($\Theta_3$ in FIG. 8); a fourth angle being the angle of inclination of the axis (115) of the shaft (110) of the nano-manipulator (140) relative to the X-Y horizontal plane (165) of the DB-FIB ($\Theta_4$ in the figures); and a fifth angle, being the angle between the projection in the X-Y plane (165) of the of the axis (115) of the probe shaft (110) and the long axis (123) of the sample (120) ($\Theta_5$ in FIG. 8), as determined by the location of the sample (120) and the rotation of the stage (170). If the sample (120) is initially in the position "A" in FIG. 8, then rotation of the stage (170) by $\Theta_5$ will place the sample (120) in the desired position "B" for lift-out. The angle $\Theta_1$ is taken to be zero when the probe shaft (110) is at the position of the sample (120) at lift out. The angle $\Theta_5$ is taken to be zero along the long axis (123) of the sample (120); $\Theta_2$ is taken to be zero when the stage is horizontal with respect to the X-Y plane (165). If the stage (170) has more than one tilt axis, then the relevant tilt axis (175) is that substantially perpendicular to the axis (195) of the ion beam (190).

We have found it convenient to use the following values for the angles described above for a Model 1540 Cross-Beam DB-FIB, manufactured by Carl Zeiss, Inc.:

$\Theta_2 = 0°$ (for stage tilt), $\Theta_3 = 140°$ (relative to the extension of the stage tilt axis nearest the front door of the DB-FIB), $\Theta_4 = 26.5°$ (for inclination of the probe shaft axis relative to DB-FIB X-Y plane).

Thus resulting in the following computed values as shown in Table 1 below:

$\Theta_1 = 104.4°$ (for desired probe shaft rotation)

$\Theta_5 = 10.1°$ (for desired stage rotation).

TABLE 1

Compute the rotation matrix of coordinates about axis of probe shaft through angle $\theta_1$, where the components of the vector representing the axis of the probe shaft are as follows (assuming unit vectors):
$k_x = \cos\theta_3 \cdot \cos\theta_4 \quad k_y = \sin\theta_3 \cdot \sin\theta_4 \quad k_z = \sin\theta_4 \quad V = 1 - \cos\theta_1$
The following exemplary angles are predetermined:
$\theta_2 = 0; \theta_3 = -140$ deg.; $\theta_4 = 26.5$ deg.
The rotation matrix for rotation about the probe shaft is therefore:

$$\mathrm{Rot}\theta_1 = \begin{pmatrix} k_x^2 \cdot V + \cos\theta_1 & k_x \cdot k_y \cdot V - k_z \cdot \sin\theta_1 & k_x \cdot k_z \cdot V + k_y \cdot \sin\theta_1 \\ k_x \cdot k_y \cdot V + k_z \cdot \sin\theta_1 & k_y^2 \cdot V + \cos\theta_1 & k_y \cdot k_z \cdot V - k_x \cdot \sin\theta_1 \\ k_x \cdot k_z \cdot V - k_y \cdot \sin\theta_1 & k_y \cdot k_z \cdot V + k_x \cdot \sin\theta_1 & k_z^2 \cdot V + \cos\theta_1 \end{pmatrix}$$

The rotation matrices for rotation about the X-axis ($\theta_2$) and the Y-axis ($\theta_5$) are:

$$\mathrm{Rot}\theta_2 = \begin{pmatrix} 1 & 0 & 0 \\ 0 & \cos\theta_2 & -\sin\theta_2 \\ 0 & \sin\theta_2 & \cos\theta \end{pmatrix} \quad \mathrm{Rot}\,\theta_5 = \begin{pmatrix} \cos\theta_5 & -\sin\theta_5 & 0 \\ \sin\theta_5 & \cos\theta_5 & 0 \\ 0 & 0 & 1 \end{pmatrix}$$

Compute a product matrix, $T = \mathrm{Rot}\theta_1 \cdot \mathrm{Rot}\theta_2 \cdot \mathrm{Rot}\,\theta_5$
$\theta_1$ is determined by the element 2,2 (index origin zero) in the matrix T when T = 0, that is, when:
$\cos\theta_2 \cdot [\cos\theta_1 + \sin\theta_4^2 \cdot (1 - \cos\theta_1)] - \sin\theta_2 \cdot [\cos\theta_3 \cdot \cos\theta_4 \cdot \sin\theta_1 + \cos\theta_4 \cdot \sin\theta_3 \cdot \sin\theta_4 \cdot (1 - \cos\theta_1)] = 0$.

TABLE 1-continued

Since $\Theta_3$ and $\Theta_4$ are predetermined, a solution for $\Theta_1$ for the exemplary values given is:
$\Theta_1 = 104.394$ deg.
Since $\Theta_1$ is now known, element 1,1 of T solves for $\Theta_5$ when T = 0, that is:
$\cos\theta_5 \cdot [\sin\theta_2 \cdot [\cos\theta_3 \cdot \cos\theta_4 \cdot \sin\theta_1 - \cos\theta_4 \cdot \sin\theta_3 \cdot \sin\theta_4 \cdot (1 - \cos\theta_1)] - \cos\theta_2 \cdot [\cos\theta_1 + (\cos\theta_4 \cdot \sin\theta_3)^2 \cdot (1 - \cos\theta_1)]] - \sin\theta_5 \cdot [\sin\theta_4 \cdot \sin\theta_1 + \cos\theta_3 \cdot (\cos\theta_4)^2 \cdot \sin\theta_3 \cdot (1 - \cos\theta_1)] = 0$.
Again, since $\Theta_3$ and $\Theta_4$ are predetermined, a solution for $\Theta_5$ for the exemplary values given is:
$\Theta_5 = 10.094$ deg.

Figure 2:
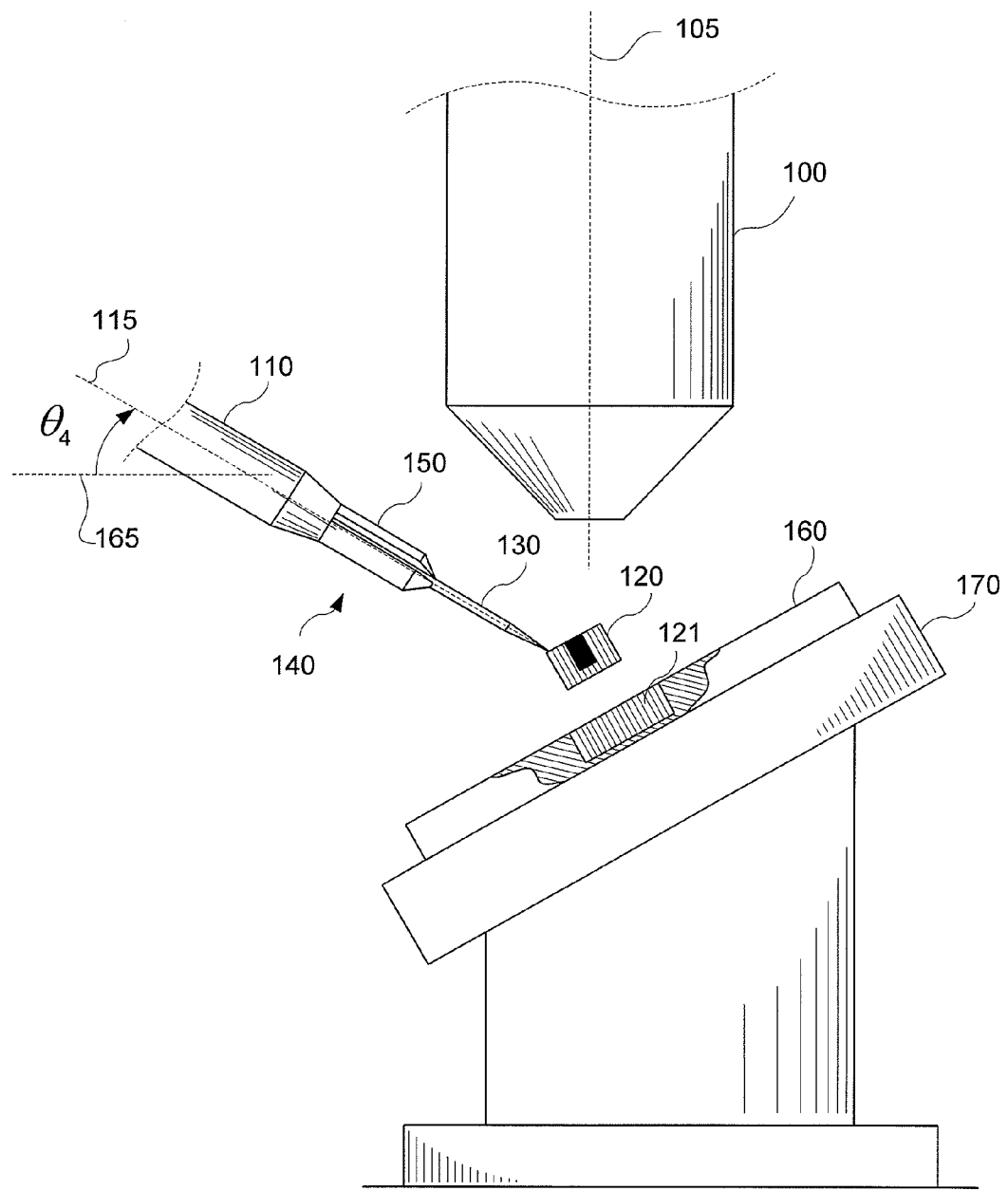
FIG. 2 shows a side view of a DB-FIB system with a TEM sample lifted out of a specimen. For clarity, only the e-beam column is shown.
Figure 3:
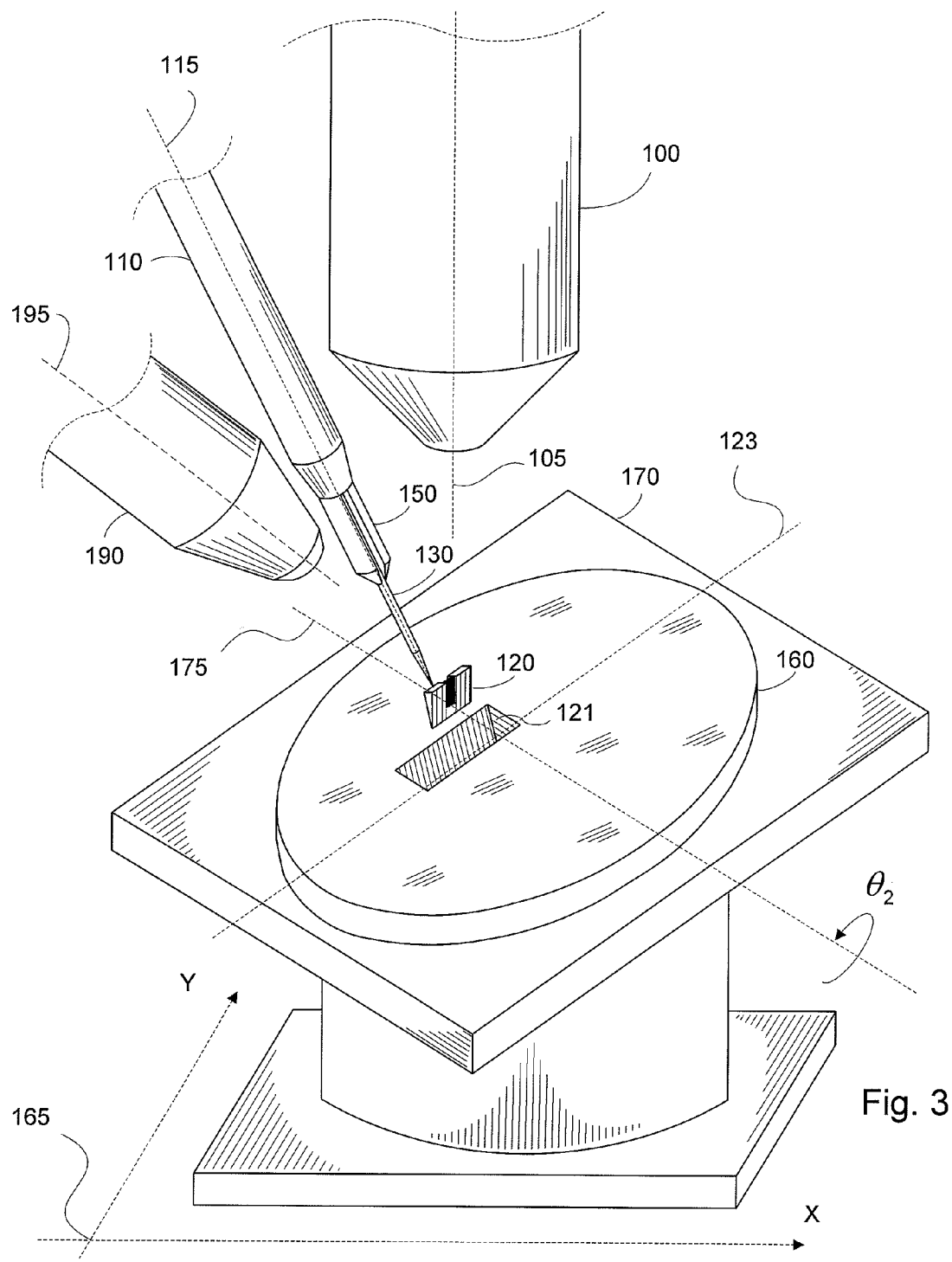
FIG. 3 shows the perspective view of a DB-FIB system with a TEM sample lifted out of the specimen (both e-beam and ion beam columns shown).
Figure 4:
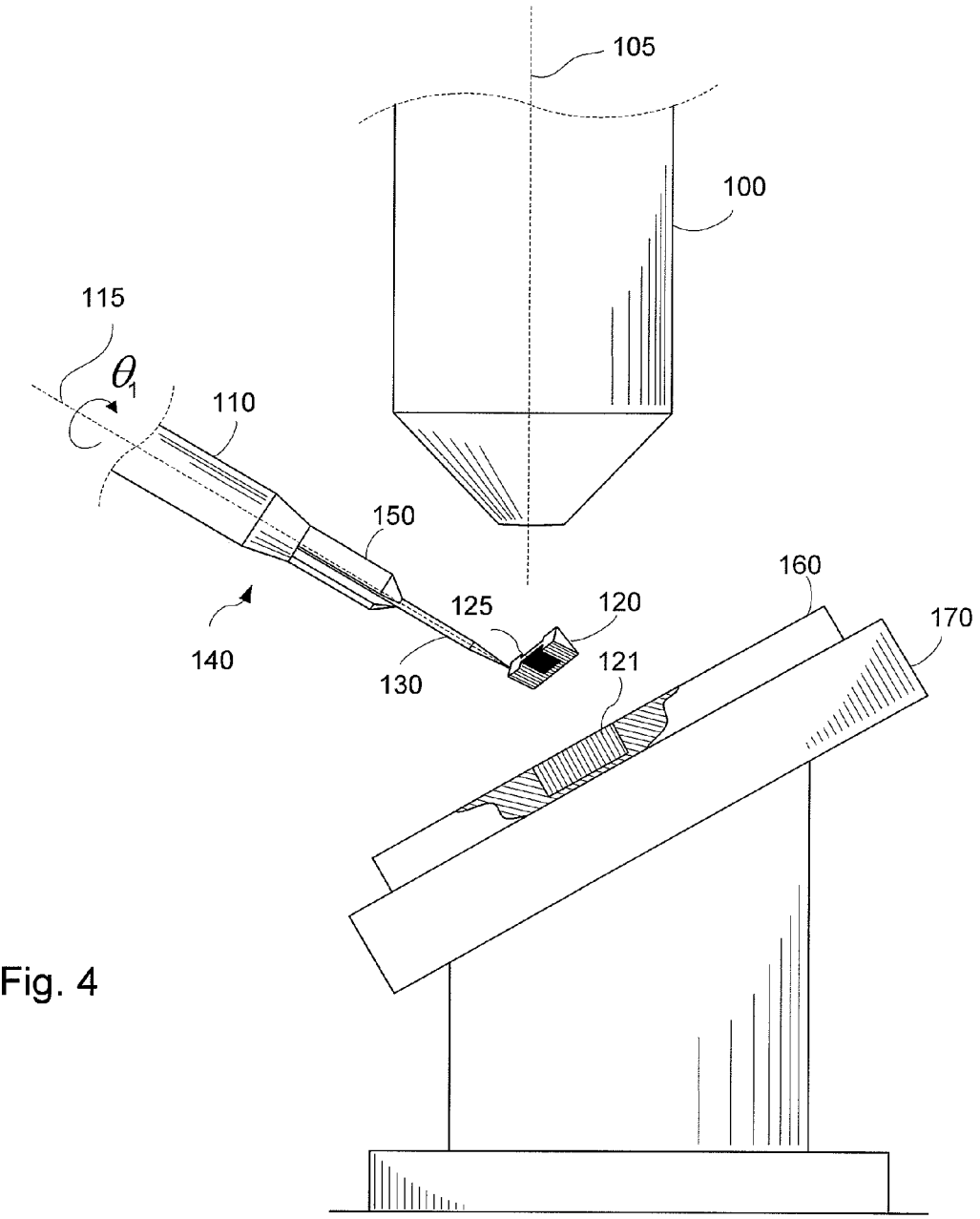
FIG. 4 shows a perspective view of a DB-FIB system with a TEM sample lifted out of a specimen. The specimen is shown thinned and partially rotated about the nano-manipulator shaft axis (only e-beam column is shown).
Figure 5:
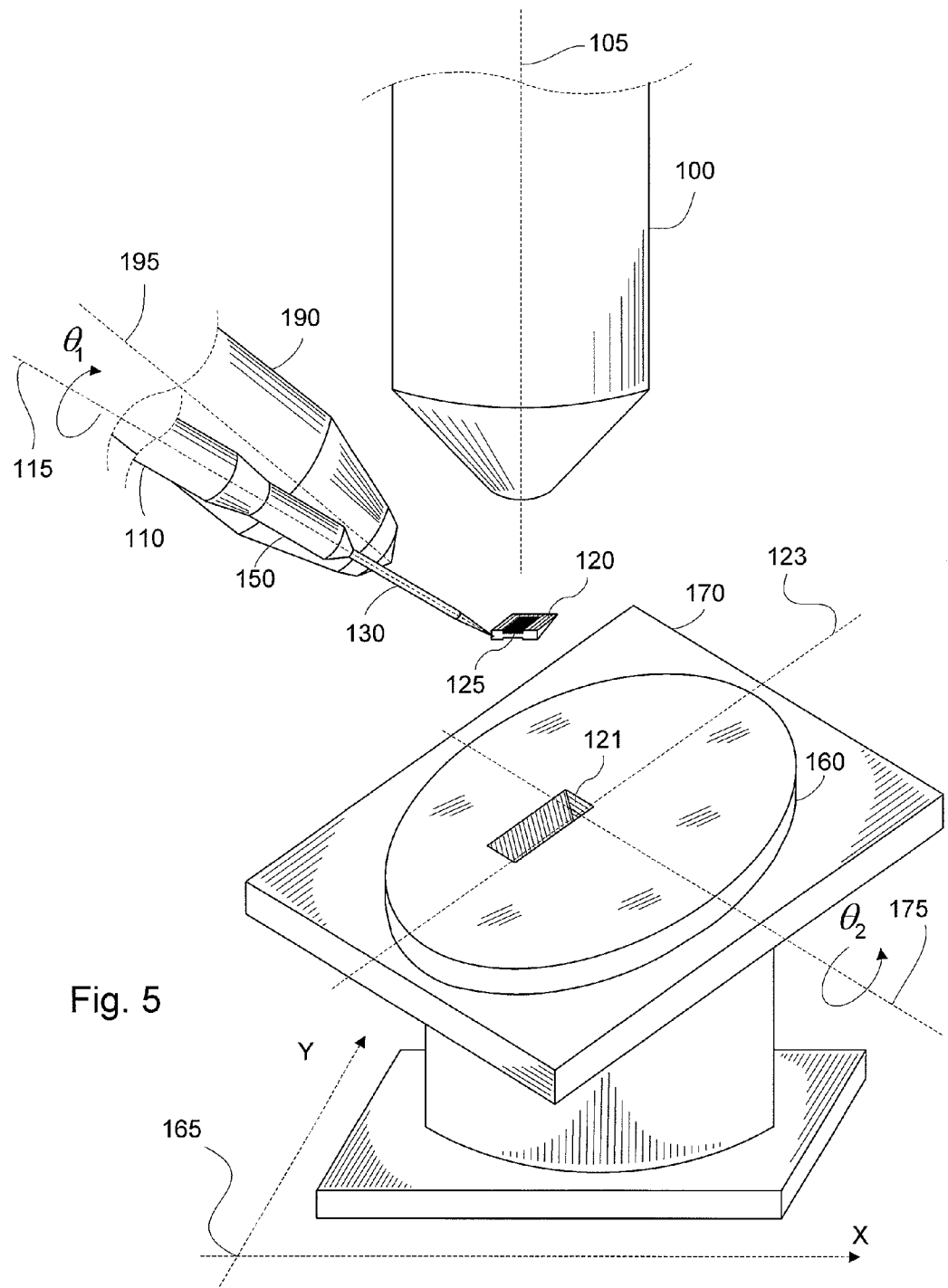
FIG. 5 shows a perspective view of a DB-FIB system with a TEM sample rotated and oriented for STEM analysis (both e-beam and ion beam columns shown).
Figure 6:
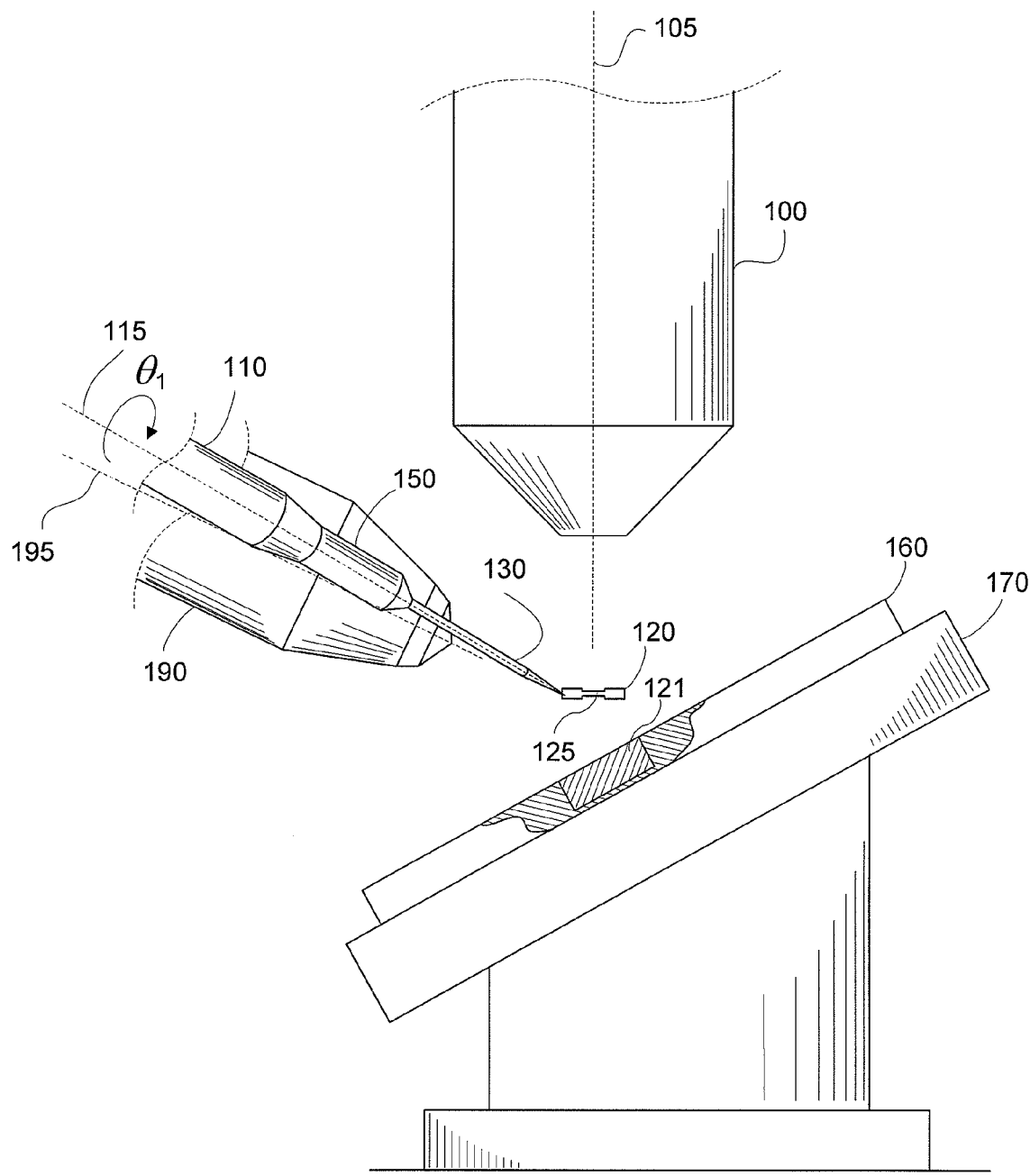
FIG. 6 shows a side view of a DB-FIB system with a TEM sample rotated and oriented for STEM analysis (both e-beam and ion beam columns shown).

The angle $\Theta_1$ is a function of $\Theta_2$-$\Theta_4$, and $\Theta_5$ is a function of $\Theta_1$-$\Theta_4$. So, in this example, given a stage (170) tilt angle of 0°, and a probe shaft inclination of 26.5°, a stage (170) rotation of approximately 10.1° will orient the sample (120), so that the sample (120), after lift-out, can be made substantially perpendicular to the vertical electron beam (100) simply by rotating the nano-manipulator probe shaft (110) by 104.4° ($\Theta_1$ in the figures). FIGS. 2 and 3 show the attachment of the probe tip (130) to the sample (120), after the stage (170) has been rotated by $\Theta_5$, followed by lift-out. FIGS. 4-6 show the rotation of the sample (120) attached to the probe tip (130) by $\Theta_1$. FIG. 6 is a side view of the sample (120) rotated into the desired orientation.

The reader should understand that the angles stated above for $\Theta_2$, $\Theta_3$, and $\Theta_4$ are exemplary only for the model of DB-FIB stated, and other angles could be used as input to the procedures set out in Table 1 to calculate the rotation of the nano-manipulator shaft (110) required to bring the sample (120) into the proper orientation for STEM imaging, both for the Zeiss DB-FIB, and instruments of other manufacturers. The pre-determined angles most convenient for a particular DB-FIB can be easily determined from the construction of the particular DB-FIB. Thus $\Theta_2$, the stage tilt is conveniently set to zero; and $\Theta_3$, the projection of the axis (115) of the probe shaft (110) relative to the axis (175) of the tilt of the stage (170), and $\Theta_4$, the inclination of the probe shaft (110) are determined by the location of the probe port and its angle with respect to the X-Y plane on the particular DB-FIB.

These calculations and operations to orient the sample stage (170) and the probe shaft (110) are preferably carried out by a programmable computer connected to suitable actuators, as described in the patent applications incorporated by reference into this application. Computer control of motors or actuators inside FIB instruments is known in the art.

Figure 7:
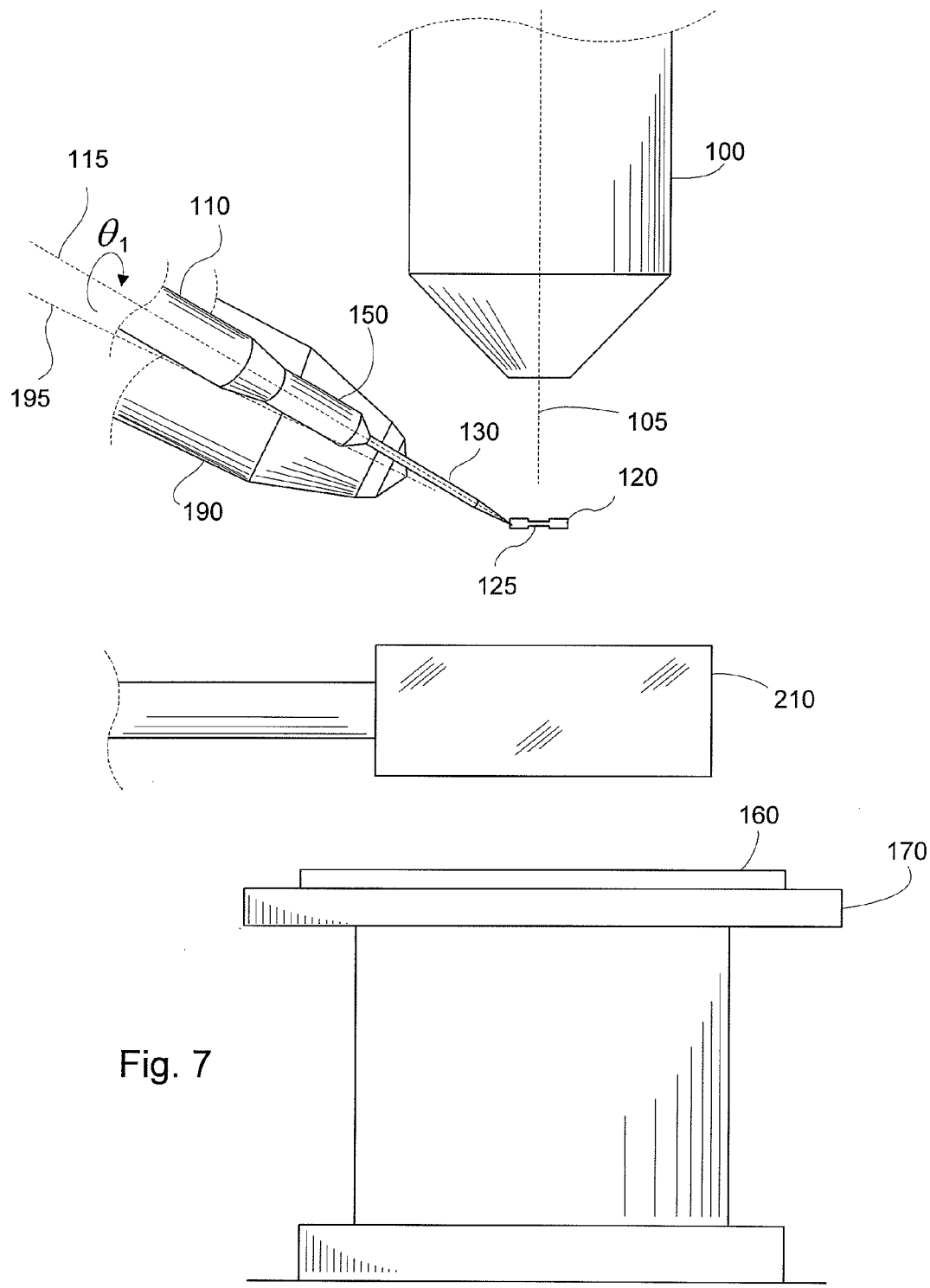
FIG. 7 shows a side view of a DB-FIB system with the specimen stage returned into a horizontal orientation and lowered, a TEM sample ready for STEM analysis, and a transmitted electron detector moved into position.

As shown in FIG. 7, a conventional transmitted electron detector (210) may be positioned and exposed in an appropriate position beneath the sample (120), so that the sample (120) can be imaged immediately in STEM mode. The position and aperture of the STEM detector (210) can be adjusted to select bright field or dark field imaging modes.

As shown in FIGS. 9-13, the sample (120) attached to the nano-manipulator probe tip (130) can be deposited into a cassette (200) located within the DB-FIB, thus enhancing its stability and allowing flexibility in positioning. The cassette (200) is typically located on the specimen stage (170) of the DB-FIB. The sample (120) is held in a very stable mechanical condition, because it is attached to the probe tip (130) when placed into the cassette (200). The position of the sample (120) in the cassette under the electron beam (100) is determined by the tilt, rotation, and X, Y and Z position of the DB-FIB specimen stage (170) at lift-out followed by the rotation of the nano-manipulator shaft, as described above, and by an additional axis of tilt of the cassette (200), if any. Therefore, the cassette (200), by having one axis of tilt normal to the DB-FIB stage (170) tilt axis (175), can provide for two essentially orthogonal tilt axes, thereby enabling any tilt orientation of the sample (120) under the electron beam (100). This dual axis tilt is preferable to, for example, a "flip stage" configuration in which only one degree of tilt is available from the DB-FIB stage (170). Tilt of the sample (120) in two degrees of freedom is often critical for obtaining the desired contrast in the STEM image. Obtaining the desired contrast in the STEM image while the sample (120) is in the DB-FIB may eliminate the need to take the sample (120) to a separate TEM or STEM instrument for inspection.

The Cassette

Figure 9:
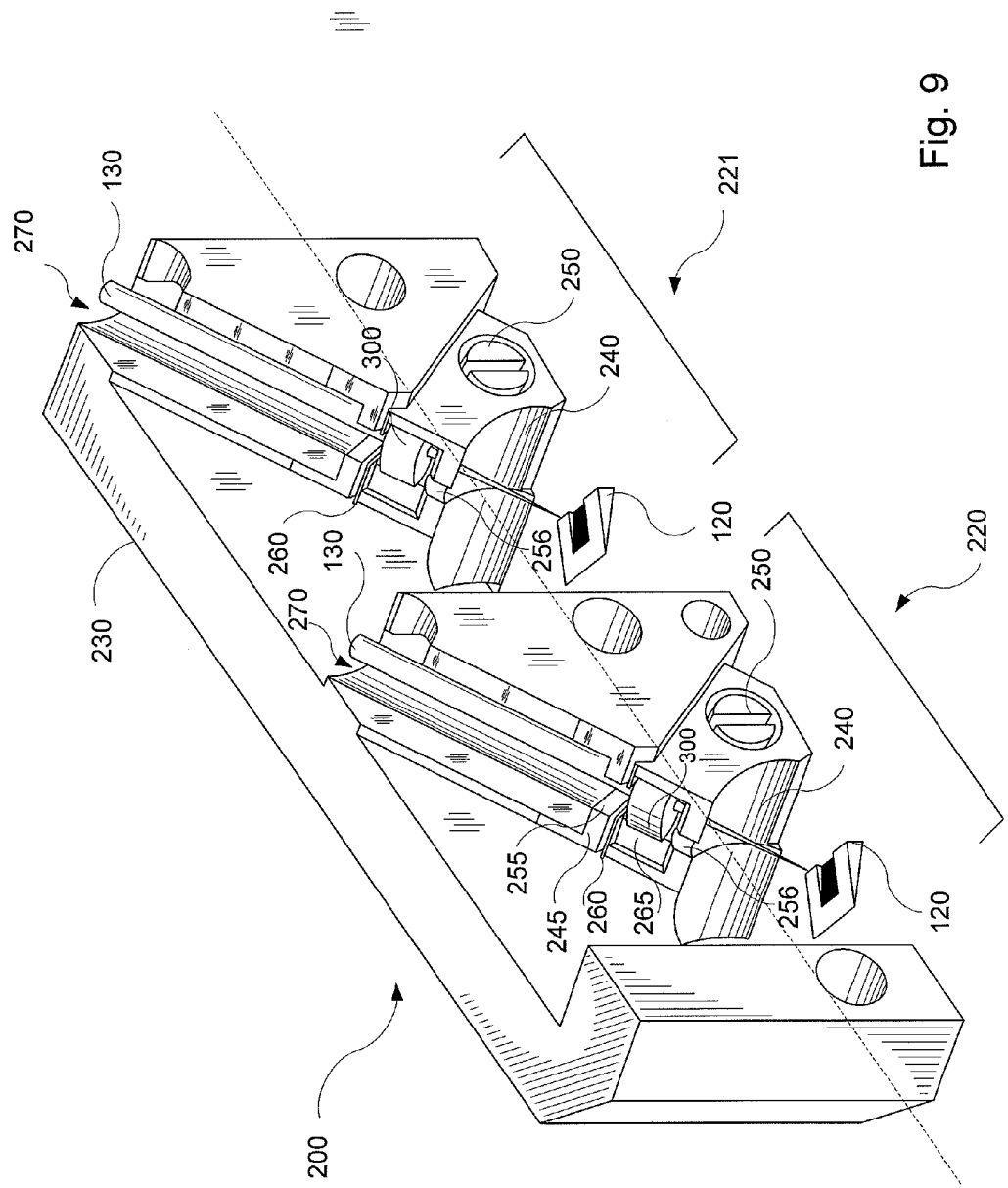
FIG. 9 shows a perspective view of a cassette containing collared probe tips with TEM samples attached.

The cassette (200) disclosed comprises a cassette base (230) and one or more probe tip stations (220, 221). The cassette (200), as depicted in FIG. 9, comprises two probe-tip stations (220), but the number of probe-tip stations (220) is not limited to two. In the embodiment shown in FIG. 9, each probe-tip station (220) comprises an insert part (240), so that the insert part (240) and the base (230) together define a collar cavity (265), for receiving a probe tip collar (300); a first cutout (255) for the shaft of the probe tip; a probe tip slot (270), for receiving the shaft of the probe tip (130); and a second cutout (256) for the probe tip (130) itself. The insert parts (240) and the base (230) are shown held by screws (250). This assembly also defines a divider portion (245) of the base (230) with the first cutout (255) in it.

Figure 10:
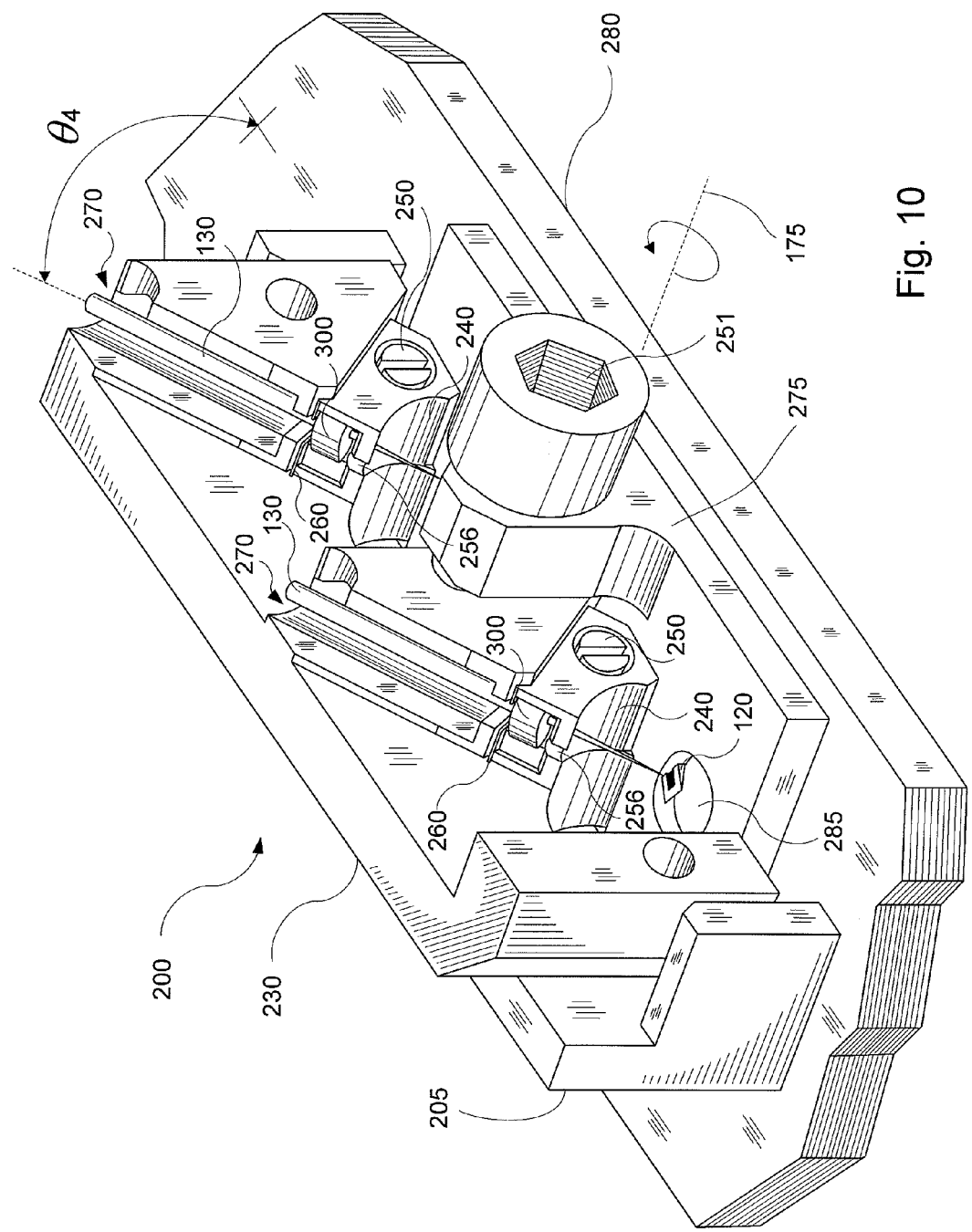
FIG. 10 shows a perspective view of a cassette containing collared probe tips with TEM samples attached. The cassette is shown mounted on a cassette holder.

FIGS. 10 and 11 show a cassette (200) connected to a cassette holder (275) by a second screw (251). In FIGS. 10 and 11, the cassette holder (275) is shown attached to a substage (280) of the specimen stage (170) that is typical of the Zeiss Model 1540 instrument referred to above. Preferably, the substage (280) has nests (205) for receiving and stabilizing the cassette (200). The angle of the probe tip slot (270) relative to the plane of the cassette holder (275) is $\Theta_4$, the same as the angle of the probe shaft (110) relative the DB-FIB X-Y plane. (The plane of the cassette holder (275) is parallel to the substage (280).) This geometry assures that the orientation of the sample (120) when placed in the probe tip slot (270) is the same as that resulting after the sample (120) is rotated according to the calculations discussed above. The angle $\Theta_4$ is shown in FIG. 10, but omitted in the other figures for clarity.

To ensure the stability of the probe tip (130) in the probe tip slot (270), a tape or film (260) with adhesive is preferably attached to the divider portion (245) to releasably capture the probe tip collar (300). A suitable material for the tape (260) is KAPTON film, with acrylic or silicone adhesive layers on both sides, available from the DuPont Corporation. The tape (260) is consumable and requires periodic replacement. The particular embodiment shown in FIG. 9 shows a probe tip (130) having a collar (300) attached to it, to ease the capture of a probe tip (130) once it is placed in the probe tip slot (270), and the collar (300) is placed in the collar cavity (265). The collar (300) can be of simple cylindrical shape or can have particular cutouts or grooves (310) in this cylindrical part (FIG. 12).

To load the probe tip (130) into a cassette probe-tip station (220), the probe tip (130), with sample (120) attached and releasably held by the gripper (150) on the probe shaft (110), is maneuvered to the vicinity of the cassette (200) by the nano-manipulator (140). The cassette (200) is mounted on the specimen stage (170) or a substage (280) in a position, so that the probe tip slot (270) is oriented at the correct angle relative to the specimen (160) surface. The probe tip (130) is moved to the probe tip slot (270) until the collar (300) is located exactly above the collar cavity (265) in the probe tip station (220). Then the probe tip (130) is lowered so the collar (300) is placed entirely inside the collar cavity (265). The nano-manipulator (140) continues moving along the probe tip (130) axis (115) so the collar (300) contacts the adhesive tape (260) and stays attached to it while the nano-manipulator (140) continues its movement, disengaging the gripper (150) from the probe tip (130). This situation is depicted in FIG. 11, where the probe tip (130) in a first probe-tip station (220) was placed in the probe tip slot (270) earlier and remains attached to the adhesive tape (260). The probe tip (130) in a second probe-tip station (221) is in the process of being placed in the probe tip slot (270). There are openings (285) in the cassette holder (275), located beneath the sample (120), to allow the immediate in-situ STEM analysis.

FIGS. 12 and 13 show a spring means (290), such as springy wire forms or leaf springs, used to capture the probe tip (130) inside the probe tip station (220). FIG. 12 shows the spring means (290) used to hold the probe tip (130) with a collar (300). FIG. 13 shows another embodiment where the spring means (290) holds a probe tip (130) without collars.

FIG. 14 shows another embodiment where the two cassettes (200) are placed into a different nest (206) attached to a different embodiment of a substage (281) for conveniently holding multiple cassettes (200). An optional sample puck (330) functions as relocatable support for specimens (320). This type of substage is typical of instruments manufactured by the FEI Company of Hillsboro, Oreg. The substage (281) shown in FIG. 14 is mounted on the FIB stage (170). This arrangement allows an additional angle of tilt of the cassette (200) (and thus the sample (120)). In FIG. 14, the substage (281) has an axis (225) of tilt substantially orthogonal to the axis of tilt (175) of the specimen stage (170). The two axes (175, 225) need not be orthogonal, but this condition simplifies the movements and calculations needed to bring the sample (120) into a desired viewing position. In other embodiments, the desired tilt of the cassette (200) may be obtained by tilting the cassette holder (275) relative to the substage (281), or, if the cassette holder (275) is attached to the specimen stage (170) itself, relative to the stage. Tilt of the substage (281) or the cassette holder (275) may be accomplished by motors or other actuators (not shown), as is known in the art for motion control inside FIB instruments.

In-Situ Stem Process Flow

FIG. 15 shows a flowchart of the method of the preferred embodiment. It starts with the system setup step 340, including the setup of the DB-FIB, nano-manipulator (140), cassette (200) and all other necessary accessories, and the location of an area of interest on the specimen (160). In step 341, the TEM lift-out sample (120) is excised from the specimen (160), thinned for STEM or TEM inspection, and released from the specimen (160). In step 342, the first and the fifth angles are calculated as described above. In step 343, the specimen stage (170) is adjusted (translated, tilted or rotated) to a position and angle as described above that will later permit the thinned portion (125) of the TEM sample to be placed perpendicular to the electron beam by a single rotation of the nano-manipulator probe shaft (110). In step 344, the probe tip (130) is attached to the pre-thinned and released sample (120) and the sample (120) is lifted-out.

In an alternative procedure, the TEM lift-out sample (120) can be excised from the specimen (160) without selective thinning to produce an electron transparent portion (125). The selective thinning can be later performed after the TEM sample (120) has been lifted out of its trench (121).

Step 341 is depicted in FIG. 1. In FIG. 1, the selectively thinned TEM sample pre-form (122) is shown cut free but remaining in its trench (121) in the specimen (160). In FIG. 2, the sample (120) is lifted out of its trench (121) and is held by the nano-manipulator (140) above the specimen stage (170). For clarity, only the electron beam (100) is shown. In FIG. 3, the perspective view of the same configuration as in FIG. 1 is shown, with both electron (100) and ion (190) beams shown. Step 345 reflects the rotation of the nano-manipulator shaft (110) through the first angle as calculated in step 342. This step is depicted in FIGS. 4 through 6. In FIG. 4, the side view of the next step of a nano-manipulator shaft (110) rotation is shown. FIG. 5 shows the following step of the preferred embodiment where the sample (120) is positioned perpendicular to the electron beam (100) so the thinned area (125) of interest can be STEM inspected. In FIG. 5, both electron (100) and ion beam (190) columns are shown. FIG. 6 shows the side view of the same sample (120) orientation.

Figure 8:
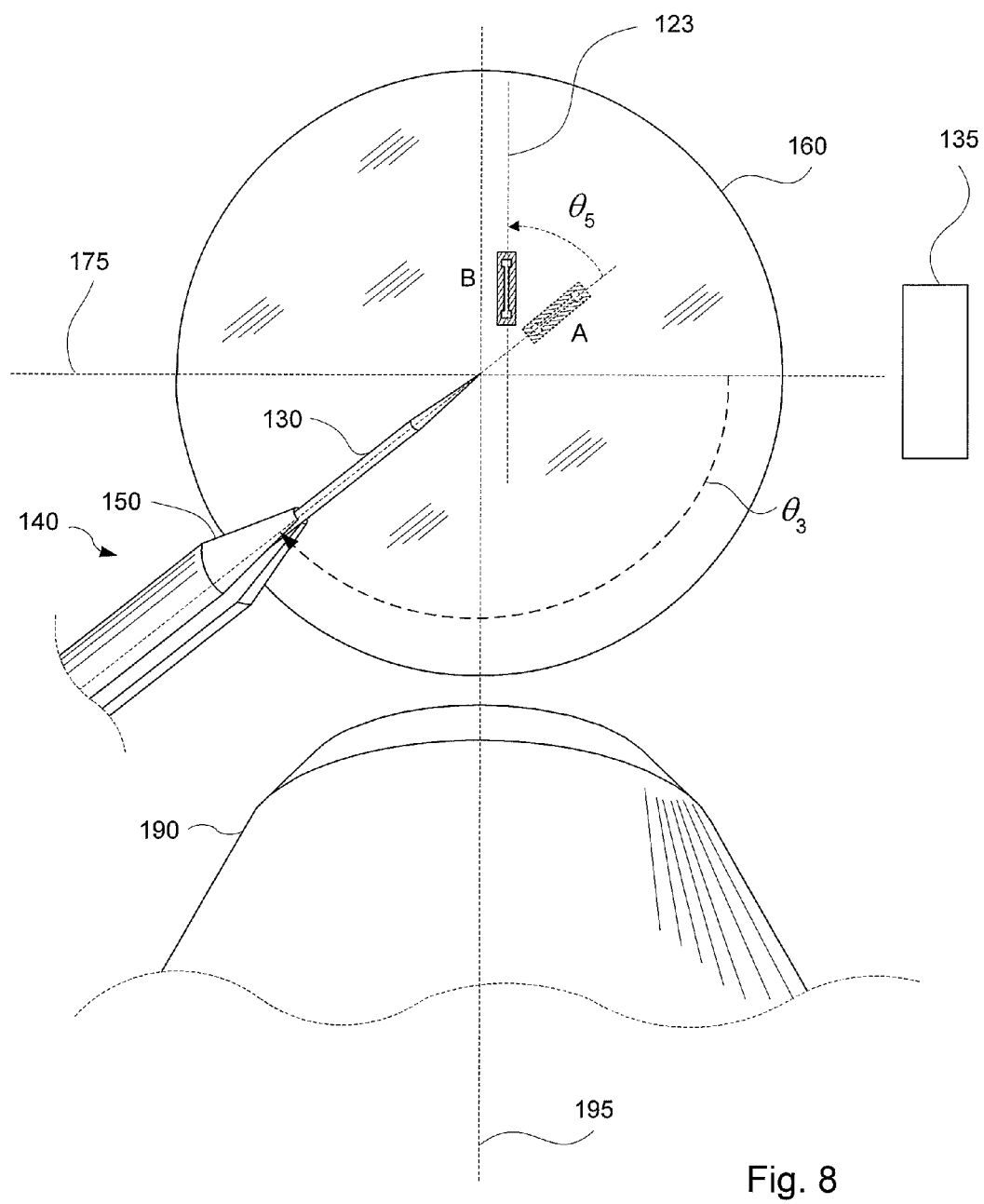
FIG. 8 shows a plan view of the horizontal plane through the sample position with the axis of the electron beam column normal to the page, and depicting the angular position of the nano-manipulator probe shaft about the electron beam axis and relative to the stage tilt axis that is perpendicular to the ion beam axis.

A decision may be made at step 346 either to perform an immediate or preliminary STEM analysis or to place the probe tip (130) with the TEM sample (120) attached, into the cassette (200). If the decision is to perform the immediate STEM analysis, the process continues in steps 353 through 358 followed by the transfer of the TEM sample (120) attached to a TEM grid (not shown) outside the FIB (step 365). FIG. 7 shows the final configuration with the sample (120) oriented perpendicularly to the electron beam (100), specimen stage (170) lowered and the transmitted electron detector (210) moved in. FIG. 8 shows a plan view from the top of the charged particle beam apparatus. The electron beam (100) is oriented vertically to the plane of the view.

After the preliminary STEM in-situ analysis on the TEM sample (120), attached to the probe tip (130), held by the nano-manipulator (140), has been performed in step 354, a decision may be made in step 355 to continue the in-situ procedure, and to proceed with the additional STEM analysis on a TEM sample (120). In step 356, the TEM sample (120) is attached to a TEM sample grid, located elsewhere on the specimen stage (170), using material deposition in the DB-FIB or other methods known in the art, followed with the separation of the probe tip (130) from the TEM sample (120) in the step 357. The additional in-situ STEM analysis of the TEM sample (120) can be performed in step 358, followed with the transfer of the TEM sample (120) attached to the TEM sample grid, outside the FIB in step 365.

Alternatively, in step 355 the decision can be made not to perform additional in-situ STEM analysis. In this case, in step 347, the probe tip (130) with the TEM sample (120) attached to it is deposited into a cassette (200) for further procedures.

Or, if the other decision has been made in step 346, the probe tip (130) can be placed into the cassette (200) immediately at step 347. Then, in the step 348, the choice is made whether to continue with the lift-out procedure for another sample (in this case the process would continue at the initial step 340), or to proceed to STEM analysis of samples (120) already placed into a cassette (200) in step 349. The specimen stage (170) is manipulated accordingly (lowered or raised) in step 349 and the in-situ STEM analysis of one or more samples is performed in step 350. The image obtained is checked for quality in step 351. If the quality is not satisfactory, the TEM sample (120) can be re-thinned tilting the stage (170) and/or the cassette (200) to the desired orientation (step 352).

After a satisfactory quality image is obtained, the process can be continued in step 359 with the choice to perform TEM analysis in a separate, standalone TEM or STEM instrument. If the choice is "No," the cassette (200) is transferred outside the DB-FIB for any necessary further procedures (step 365). If the choice is "Yes," then in step 360 the probe tip (130) with the TEM sample (120) attached to it is captured again with the gripper (150) and returned to its original orientation in step 361 using rotation of the probe shaft (110) as described above, followed with the adjustment of the TEM grid orientation in step 362. Then in step 363 the TEM sample (120) can be attached to the TEM grid using material deposition in the DB-FIB, or other conventional methods, followed with the separation of the probe tip (130) from the TEM sample (120) in step 364. Thereafter, the TEM grid with the TEM samples attached to it can be transferred outside the DB-FIB for further investigation in step 365.

This embodiment comprises a set of repeated operations and is appropriate for an automated procedure. It can be the part of the probe-tip exchange procedure described in co-pending U.S. patent application Ser. No. 11/186,073, which in turn is the part of the automated lift-out procedure described in the co-pending automated lift-out procedure (U.S. application Ser. No. 11/265,934). The method described is not limited to DB-FIB instruments with a fixed relationship between the electron (100) and ion (190) beam columns. The method can be practiced on an instrument with the ability to tilt one or both beams relative to the specimen stage (170).

The method described can be also used in an apparatus for lift-out where a laser beam (180) is used in addition to or instead of the ion beam. An embodiment is shown in FIG. 16, where the laser beam (180) and the gas injector apparatus (185) are schematically shown. In this embodiment, the laser beam (180) is used to pre-cut the sample (120) from the wafer possibly using gas chemistries provided by the gas injector (185) and possibly using a mask (not shown) followed by thinning performed by ion beam (190). The laser beam (180) and the ion beam (190) may reside in the same chamber or in separate chambers.

Since those skilled in the art can modify the specific embodiments described above, we intend that the claims be interpreted to cover such modifications and equivalents.

We claim:

1. A method for examination of an excised sample in a charged particle beam instrument, where the sample has a long axis, and where the charged particle beam instrument comprises:
   an ion-beam;
   a specimen stage;
      the specimen stage having at least one tilt axis substantially perpendicular to the axis of the ion beam;
   an electron beam;
      the electron beam having an axis; and,
   an X-Y plane;
   a nano-manipulator; the nano-manipulator having a probe shaft; the probe shaft having an axis;
      the probe shaft further having a probe tip;
   where the method comprises:
   calculating a first angle as a function of:
      a pre-determined second angle that is the angle of tilt of the specimen stage relative to the X-Y plane of the charged particle beam instrument;
      a pre-determined third angle that is the angle between the tilt axis of the specimen stage and the projection onto the X-Y plane of the axis of the probe shaft; and,
      a pre-determined fourth angle that is the inclination of the axis of the probe shaft relative to the X-Y plane of the charged particle beam instrument;
   calculating a fifth angle as a function of the first, second, third, and fourth angles, where the fifth angle is the angle between the long axis of the sample and the projection of the axis of the probe shaft onto the X-Y plane;
   rotating the specimen stage to the calculated fifth angle, whereby the projection of the axis of the probe shaft onto the X-Y plane is collinear with the long axis of the sample;
   attaching the sample to the probe tip;
   lifting out the sample with the probe tip; and,
   rotating the probe shaft by the calculated first angle, whereby the sample is placed substantially perpendicular to the axis of the electron beam.

2. The method of claim 1, further comprising imaging the sample by a placing a transmitted electron detector beneath the sample.

3. The method of claim 1, further comprising:
   attaching the sample to a TEM grid;
   separating the attached sample from the probe tip; and,
   carrying out STEM analysis on the sample while it is attached to the TEM grid.

4. The method of claim 3, further comprising:
   transferring the TEM sample grid with TEM sample attached to it, outside the charged particle beam instrument.

5. The method of claim 1 where calculating the first angle and the fifth angle comprises transforming an angle-axis representation of the first, second, third, fourth and fifth angles to a rotation matrix representation.

* * * * *